(12) United States Patent
Maranhao et al.

(10) Patent No.: US 12,268,606 B2
(45) Date of Patent: Apr. 8, 2025

(54) AUTONOMOUS HYDROGEN EVOLUTION REACTION THRESHOLD DETECTION METHOD AND DEVICE

(71) Applicant: Garwood Medical Devices, LLC, Buffalo, NY (US)

(72) Inventors: Jason M. Maranhao, Warwick, RI (US); Brian R. Peterson, East Aurora, NY (US); Jackson G. Hobble, Buffalo, NY (US); Mary K. Canty, Tonawanda, NY (US)

(73) Assignee: Garwood Medical Devices, LLC, Buffalo, NY (US)

( * ) Notice: Subject to any disclaimer, the term of this patent is extended or adjusted under 35 U.S.C. 154(b) by 492 days.

(21) Appl. No.: 17/616,448

(22) PCT Filed: Jun. 3, 2020

(86) PCT No.: PCT/US2020/035815
§ 371 (c)(1),
(2) Date: Dec. 3, 2021

(87) PCT Pub. No.: WO2020/247422
PCT Pub. Date: Dec. 10, 2020

(65) Prior Publication Data
US 2022/0313439 A1  Oct. 6, 2022

Related U.S. Application Data (60) Provisional application No. 62/856,282, filed on Jun. 3, 2019.

(51) Int. Cl.
*A61F 2/30* (2006.01)
*A61F 2/46* (2006.01)
(Continued)

(52) U.S. Cl.
CPC .......... *A61F 2/30* (2013.01); *A61N 1/025* (2013.01); *A61N 1/08* (2013.01); *A61N 1/205* (2013.01);
(Continued)

(58) Field of Classification Search
CPC ........................................ A61F 2002/30719
See application file for complete search history.

(56) References Cited

U.S. PATENT DOCUMENTS

| 5,458,627 A | 10/1995 | Baranowski, Jr. et al. |
| 9,616,142 B2 | 4/2017 | Ehrensberger et al. |

(Continued)

FOREIGN PATENT DOCUMENTS

| CN | 103952305 A | 7/2014 |
| JP | 2015-007291 A | 1/2015 |

(Continued)

OTHER PUBLICATIONS

Dargahi et al (Investigating electrochemical removal of bacterial biofilms from stainless steel substrates, Colloids and Surfaces B: Biointerfaces, 117, 2014, pp. 152-157). (Year: 2014).*

(Continued)

*Primary Examiner* — Alexander W Keeling
(74) *Attorney, Agent, or Firm* — Barclay Damon LLP (57) ABSTRACT

A method and apparatus to autonomously analyze the surface area and alloy composition ratios of a metallic implant, such as an orthopedic implant, so that an optimal voltage for biofilm disruption can be selected and make treatment easier based at least in part upon the autonomous detection of a hydrogen evolution reaction threshold.

19 Claims, 5 Drawing Sheets

(51) Int. Cl.
    *A61N 1/02*     (2006.01)
    *A61N 1/08*     (2006.01)
    *A61N 1/20*     (2006.01)

(52) U.S. Cl.
    CPC ............... *A61F 2002/30719* (2013.01); *A61F 2002/4674* (2013.01); *A61F 2310/00017* (2013.01); *A61F 2310/00023* (2013.01); *A61F 2310/00029* (2013.01)

(56) References Cited

U.S. PATENT DOCUMENTS

| | | |
|---|---|---|
| 2011/0029080 A1 | 2/2011 | Gilbert |
| 2016/0000947 A1 | 1/2016 | Brodbeck |
| 2017/0000918 A1 | 1/2017 | Ehrensberger et al. |
| 2018/0207301 A1 | 7/2018 | Beyenal |

FOREIGN PATENT DOCUMENTS

| | | |
|---|---|---|
| JP | 2016-504949 A | 2/2016 |
| WO | 2018/165118 A1 | 9/2018 |

OTHER PUBLICATIONS

International Search Report and Written Opinion for PCT/US2020/035815; Dated: Aug. 28, 2020; 9 pages.

Investigating electrochemical removal of bacterial biofilms from stainless steel substrates; M. Dargahi et al.; Colloids and Surfaces B: Biointerfaces 117; journal homepage: www.elsevier.com/locate/colsurlb; 6 pages (152-157); ©2014.

Antibiotics Enhance Prevention and Eradication Efficacy of Cathodic-Voltage-Controlled Electrical Stimulation against Titanium-Associated Methicillin-Resistant *Staphylococcus aureus* and *Pseudomonas aeruginosa* Biofilms; M. Canty et al.; mSphere American Society for Microbiology; https://msphere.asm.org; vol. 4/Issue 3; 14 pages; ©2019.

Cathodic Electrical Stimulation Combined With Vancomycin Enhances Treatment of Methicillin-resistant *Staphylococcus aureus* Implant-associate Infections; S. Nodzo et al.; Clinical Orthopaedics and Related Research; 9 pages (2856-2864); ©2015.

Canadian Intellectual Property Office; Canada's First Examiner's Report; Canadian Patent Application No. 3,138,562 based on International Application No. PCT/US20/035815; Dated: Mar. 13, 2023.

Japanese Intellectual Property Office; First Office Action; Japanese Application No. 2021-571630; Mailing Date: Apr. 25, 2023; 4 pages.

Mahdi Dargahi et al.; Investigating Electrochemical Removal of Bacterial Biofilms from Stainless Steel Substrates, Colloids and Surfaces B: Biointerface; Feb. 20, 2014, vol. 117, pp. 152-257; https://www.sciencedirect.com/science/article/abs/pii/S0927776514000885.

European Patent Office; Extended European Search Report; European Application No. 20819299.7; Dated: Sep. 19, 2023; 7 pages.

\* cited by examiner

AUTONOMOUS HYDROGEN EVOLUTION REACTION THRESHOLD DETECTION METHOD AND DEVICE

CROSS REFERENCE TO RELATED APPLICATION

This application is a national stage application under 35 U.S.C. § 371 of International Application No. PCT/US2020/035815, filed Jun. 3, 2020, which claims priority under applicable portions of 35 U.S.C. § 119 to U.S. Patent Application Ser. No. 62/856,282, filed Jun. 3, 2019, the entire contents of each application being herein incorporated by reference herein.

TECHNICAL FIELD

This application is generally directed to the field of treatment systems for metallic implants, and more specifically directed to an apparatus and related method for controlling an applied voltage of a cathodic voltage controlled electrical stimulation (CVCES) treatment system.

BACKGROUND

Metal implants are orthopedic devices or apparatus that are used in patients with many different injuries or medical problems. In particular, metal implants may be used for any individual that needs to replace joints. For example, a metal implant may be used to replace a patient's hips or knees. One potential problem with metal implants is that they tend to allow for the growth of bacteria on the surface. This may increase the patient's risk for an infection, which could require the potential removal of the implant. To decrease the risk of infection, electrodes can provide electrical stimulation to disrupt the growth of bacteria.

It has been shown in scientific literature that application of cathodic current to metal samples create chemical reactions at that surface that can disrupt and kill bacterial biofilms that exist on the metal. For electrochemical processes to occur, there must be an anode and a cathode within an electrolyte solution. The anode is a metallic surface where oxidative reactions occur, and the cathode is another metallic surface where reduction reactions occur. A reduction reaction is essentially when the material of interest gains electrons and thereby decreases the oxidation state of the molecules. The electrolyte that the anode and cathode each reside in provides the electrical connection by facilitating the flow of electrons shuttled by ion carriers, such as sodium or potassium ions. Electrons are driven from the anode to the cathode through the electrical path via a potentiostat.

A potentiostat is a stimulating device or instrument used to drive electrical current from a counter electrode to a working electrode in order to keep the voltage on the working electrode at a constant value, as compared to a stable reference electrode. In the case of Cathodic Voltage Controlled Electrical Stimulation (or CVCES), the anode represents the counter electrode and the cathode represents the working electrode. Using a potentiostat, a user can dictate which electrochemical process is actually occurring on the working electrode and at what rate it occurs simply by adjusting the applied voltage parameters.

The CVCES technique in a clinical setting has been shown as a way to fight bacterial biofilm infections on metallic implants in the most minimally invasive way possible. In this setting, the patient's body acts as an electrochemical cell by using the metal implant (working electrode) as the cathode and the counter electrode as the anode.

To that end, metallic orthopedic implants are typically fabricated from a combination of various alloys that demonstrate different electrochemical properties in relation to one another. In general, virtually all alloys used in orthopedic implants passively form an oxide layer on their surface while residing at internal body conditions. This oxide layer provides the metals with their high biocompatibility characteristics. When applying cathodic voltages to these oxide layers with a potentiostatic treatment, the oxide layers of different alloys will behave differently compared to each other mainly in terms of their respective current draw. In addition, orthopedic implants possess varied ratios of exposed surface area with respect to each alloy. Therefore and when the material composition is unknown, a single CVCES treatment at a blindly or randomly selected voltage would ultimately elicit a very unpredictable electrochemical response that may not be optimal for biofilm disruption.

Accordingly, there is a need in the field for a treatment technique that can autonomously analyze electrochemical indicators to identify alloy composition ratios of a surgical metal implant in order to select an optimal stimulation voltage for biofilm disruption, thereby minimizing the chances for human error, and making the treatment ultimately easier to implement for the physician or nurse.

BRIEF DESCRIPTION

Thus and to address this prevailing need, a technique has been devised based on autonomous detection of hydrogen evolution reaction and more specifically a hydrogen evolution threshold. More specifically, the detection of a hydrogen evolution reaction threshold addresses the problem of setting an optimal voltage stimulation by autonomously reading a potentiodynamic cathodic polarization scan or curve to select an optimal voltage for purposes of treatment. Each surgical metal implant naturally will demonstrate its own unique polarization curve, depending on its ratio of exposed alloys in the electrochemical environment as would be created for a CVCES treatment. The techniques described in this application can be applied to any metallic implant by autonomous detection of one or more common indicators that are based on the shape of the polarization curve in order to calculate the optimal voltage.

A potentiodynamic polarization scan is a potentiostat-based technique commonly used in electrochemistry to study fundamental behaviors at the anode and cathode interfaces. This technique can be applied in either an anodic direction or in a cathodic direction. In CVCES treatment systems, a cathodic polarization scan is implemented that essentially induces a neutral or near zero voltage upon the metal implant and incrementally increases the voltage in the negative direction over set time intervals. A current is measured that corresponds to each voltage. When working with passivated metallic alloys, the resulting graph of current values will always form the same fundamental shape. This shape can be explained further by understanding the electrochemical reactions that facilitate the electron transport. There exists a particular indicator in the polarization curve that represents the threshold at which hydrogen begins to evolve from the water reduction reaction. Biofilm disruption is maximized at levels of current that are more cathodic to this threshold due to the synergistic effects of metal-bacterial charge repulsion and local pH increase provided by the reduced water molecules. However, if the voltage increases cathodically or in the negative direction too far below this threshold, this may cause current levels and pH increases that can cause necrosis in the surrounding tissue. There is scientific evidence that shows what levels of current density are optimal for biofilm disruption cathodic to the hydrogen evolution threshold. However, Applicant has realized by detection of that threshold, one may pinpoint, that is determine, how much further to increase the stimulation voltage in order to maintain safety and effectiveness. There is also scientific evidence that once the above threshold has been met, a certain amount of cumulative charge transfer through the metal surface, measured in coulombs, can be effective in eliminating the biofilm at any current density that is not histologically harmful to the surrounding tissue.

According to one aspect, there is provided a method of providing cathodic voltage controlled electrical stimulation comprising the steps of: providing a metallic object to be treated that serves as a working electrode; applying a polarization scan to the metallic object to be treated; using a processor, autonomously detecting a hydrogen evolution reaction threshold from the polarization scan to determine a cathodic voltage to be applied to the object to be treated; and, applying the determined cathodic voltage to the metallic object to be treated.

According to another aspect, there is provided a device for controlling a cathodic stimulation voltage for treatment of a metallic object, the device comprising a processor configured for connection to a potentiostat; working, counter and reference electrodes coupled to the potentiostat, wherein the working electrode is the metallic object to be treated; wherein the processor is programmed to: apply a polarization scan to the metallic object to be treated and generate polarization data; using the processor, autonomously detect a hydrogen evolution reaction threshold from the generated polarization data for determining a cathodic voltage to be applied to the metallic object to be treated for removal of biofilm; and, apply the determined cathodic voltage to the metallic object to be treated.

The methods disclosed herein include time-based calculations in which the voltage is varied, and the current is measured after a set block of time. Once the hydrogen evolution threshold is identified via the resulting polarization scan, a suitably programmed device may proceed with either of two (2) modes in order to select an appropriate treatment voltage. In accordance with one mode, the user may input the surface area of the object (implant) to be treated, if available, and based on this surface area, the current density can be calculated. According to this mode and when the current density is at or above a prescribed target, the applied voltage is used for the remainder of the treatment. Alternatively and in the second mode, the device can be set to run a treatment in terms of charge transfer that does not require knowledge of a specific surface area for inputting. Once the alloy type of the implant is detected based on aspects of a polarization scan, the device may select a recommended voltage cathodic to the hydrogen evolution threshold of the scan that will be applied to the implant for treatment to completion. According to this latter mode, the recommended voltage is applied until a specific charge transfer has been reached.

DETAILED DESCRIPTION

The following description relates to embodiments for an apparatus and a related method for obtaining an optimal voltage stimulation point for a CVCES implant treatment system. Throughout this disclosure, a number of terms are used in order to provide a suitable frame of reference with regard to the accompanying drawings. These terms, which include "first", "second", "third", and the like should not be interpreted to overly narrow the invention, except where so specifically indicated.

Figure 1:
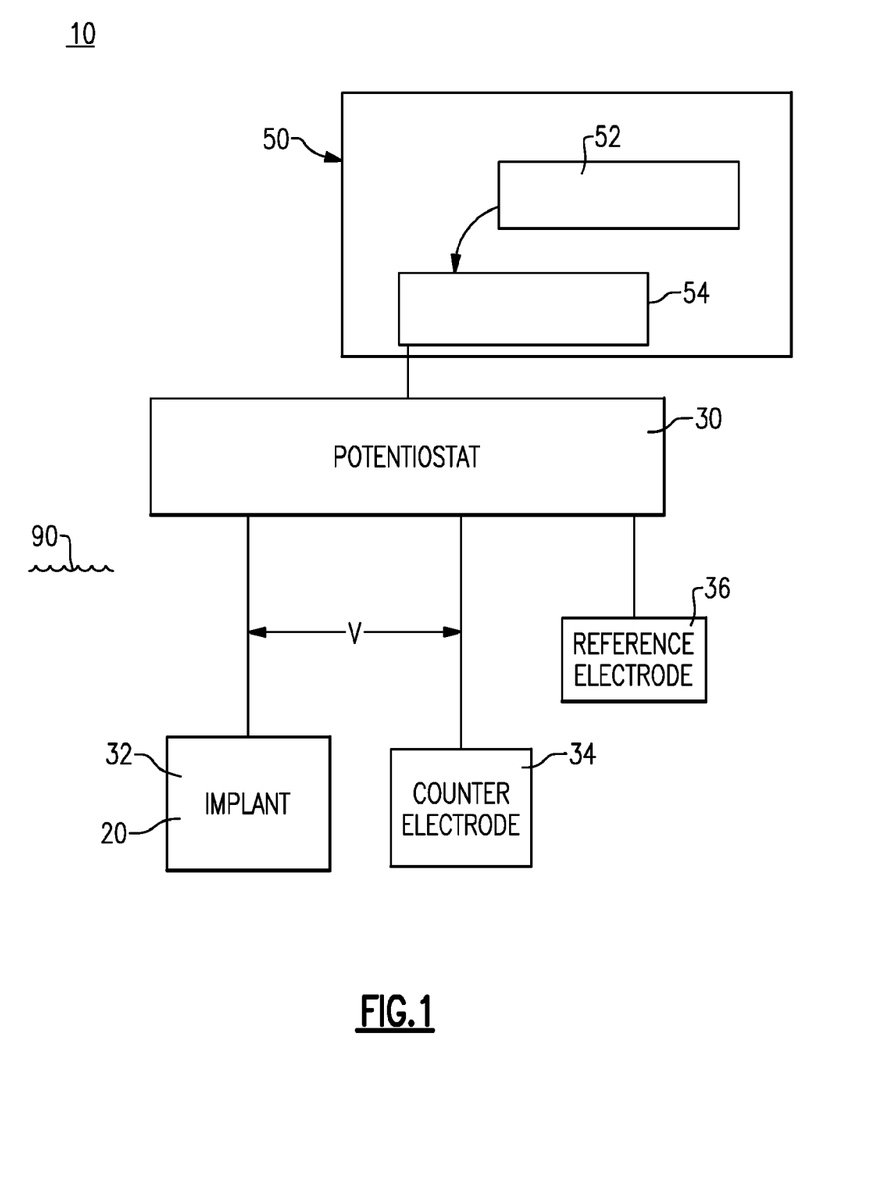
FIG. 1 schematically depicts a CVCES implant treatment system that has been configured with a suitably programmed autonomous hydrogen evolution reaction threshold detection device.

With reference to FIG. 1, there is shown a CVCES treatment system 10 that is configured in accordance with an exemplary embodiment. As noted and in order for electrochemical processes to occur, there must be an anode and a cathode within an electrolyte solution. The anode is a metallic surface where oxidative reactions occur, and the cathode is another metallic surface where reduction reactions occur. A reduction reaction is essentially when the material of interest gains electrons and thereby decreases the oxidation state of the molecules. The electrolyte that they each reside in provides the electrical connection by facilitating the flow of electrons shuttled by ion carriers, such as sodium or potassium ions. In the depicted treatment system 10, electrons are driven from the anode to the cathode through the electrical path above via a potentiostat 30.

The potentiostat 30 or similar device capable of producing an electrical potential is electrically coupled to a metal implant, schematically labeled by reference numeral 20. The metal implant 20 can for example, be a knee, hip, shoulder or other orthopedic replacement, or can further include other surgically implanted devices, such as, for example, dental implants. The implant 20 forms the working electrode 32 of the herein described CVCES treatment system 10. A counter electrode 34 is positioned in the vicinity of the working electrode (implant 20) and coupled to the potentiostat 34 along with the reference electrode 36, the latter being made from Ag/AgCl or other suitable biocompatible and electrically conductive material, each linked through an appropriate circuit to one another and to the potentiostat 30. Additional details relating to CVCES treatment are described in U.S. Pat. No. 9,616,142, the entire contents of which are incorporated by reference.

The potentiostat 30 is an instrument used to drive current from a counter electrode 34 to the working electrode 32 in order to keep the voltage on the working electrode 32 at a constant value compared to the stable reference electrode 36. In the case of a cathodic voltage controlled electrical stimulation treatment system, such as system 10, the anode represents the counter electrode 34 and the cathode represents the working electrode 32, which as noted, is typically the metal implant 20 itself.

Shifting our focus to metallic biomaterials that are often used as implants 20 in the human body, almost every metallic biomaterial thermodynamically favors a passivated state when residing at internal body temperature and pH. In almost all cases, this passivated state consists of oxygen chemically bonding with the metal to form a thin oxide layer over the top of the metal that gives it resistance to corrosion. This oxide layer provides the metallic materials with biocompatible characteristics, enabling these materials to be considered a "biomaterial". Some examples of the most common metallic biomaterials used in orthopedic implants include titanium alloys, stainless steel, and cobalt-chromium alloys.

The goal of the CVCES treatment system, as described in U.S. Pat. No. 9,616,142, is to apply a cathodic voltage to the oxide layer of a surgical metal implant to elicit a certain electrochemical reaction on the surface of that metal that will disrupt bacteria and biofilms through a faradic charge transfer process, a non-faradaic charge transfer process, and a pH elevation. It has been studied that greater negative voltages decrease the interfacial resistance to electron transfer and increases capacitance in the oxide layer, which facilitates a large negative charge build up on the surface of the metal that can then repel and disrupt bacteria and biofilms. In addition, the combination of OH— molecules raising local pH and hydrogen gas forming on the surface of the implant synergistically disturb the bacteria's metabolism. However, voltages that are too negative can accelerate these electrochemical responses to a level that can harm the surrounding tissue and cause mild necrosis. Since each metallic biomaterial responds differently to cathodic stimulation, known treatment systems such as described in U.S. Pat. No. 9,616,142 require another degree of intelligence or processing in order to safely and effectively disrupt bacterial biofilms on implants that are complex or are fabricated from a composite alloy(s).

Due to different natural characteristics of metallic biomaterials including standard reduction potential, open circuit potential, and Bulter-Volmer kinetics, the same electrochemical response may not be present from material to material at a given cathodic potential. For example and at a given voltage, a titanium alloy sample may draw a low current and may still be operating on the oxygen reduction reaction. Conversely, a cobalt-chromium alloy will draw a much higher current and facilitate hydrogen gas formation at the same cathodic voltage. To make things more complex, exact electrochemical processes become more unpredictable when implants are composed of two or more metallic surface materials with varying surface area ratios. The surface finish of each metal implant also becomes a factor as surfaces with a higher grit finish (more polished) elicit a slower electrochemical reaction due to their lower surface area, as compared to a metal with a low grit finish (rough and unpolished). As of present, scientific evidence shows efficacy of a cathodic voltage controlled electrical stimulation on commercially pure titanium samples at a voltage of −1.8 Volts because the electrochemical reaction is well known, and the current density has been precisely measured. However, a stimulation point of −1.8 Volts will not, in almost all instances, work safely and consistently for all metals. It has been found that in general, titanium implants should typically be stimulated with −1.8 Volts to −2.0 Volts for optimal disruption, where other alloys like cobalt chromium and stainless steel are typically optimal in the −1.5 Volt to −1.7 Volt range vs. Ref (typically Ag/AG-Cl). As mentioned, stimulating at levels more cathodic to these ranges may cause higher degrees of damage to tissue and could completely dissolute the biocompatible oxide layer from the surface of the metal.

Referring back to FIG. 1 and using the potentiostat 30, a user can dictate which electrochemical process is actually occurring on the working electrode 32 and at what rate it occurs simply by adjusting the applied voltage parameters. However, if the user does not know at what voltage threshold specific reactions halt or begin at, it becomes very difficult to elicit a precision reaction and reaction rate.

The potentiodynamic polarization scan is a technique commonly used in electrochemistry to study fundamental behaviors at the anode and cathode interfaces and is a staple tool standard to most modern potentiostats. The polarization scan can be applied in either an anodic direction or in a cathodic direction. Typical cathodic voltage controlled electrical stimulation of metal implants focuses on applying negative voltages, therefore the herein described device and associated method utilizes a cathodic polarization scan.

Figure 2:
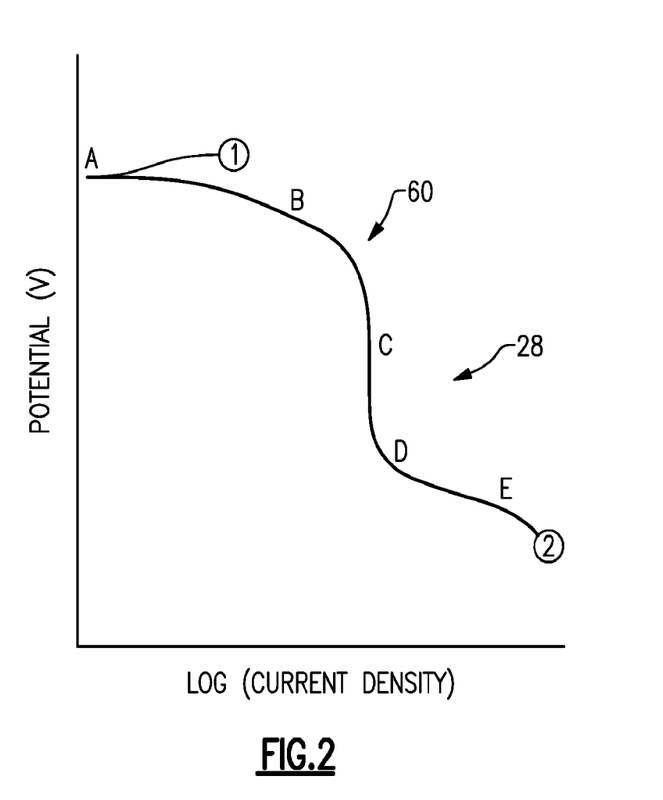
FIG. 2 is a typical cathodic polarization scan depicting electrical potential (volts) versus a log of current density.

A cathodic polarization scan 28 for a typical metal is illustrated in FIG. 2 graphically depicting electric potential (voltage) against current density, the latter shown logarithmically. In the depicted cathodic potentiodynamic scan 28, an applied electrical potential from a potentiostat is varied from point 1 in the negative direction to point 2. The open circuit potential (OCP) is located at point A. The OCP represents the potential at which the sum of the anodic and cathodic reactions occurring on the working electrode surface 24 is zero. Depending on the pH and dissolved oxygen concentration in the electrolytic solution 90, FIG. 1, region B represents the range at which the oxygen reduction reaction, FIG. 3, dominates electron transfer. Since this latter reaction is limited by how fast oxygen can diffuse in solution, there exists an upper limit on the rate of this reaction, known as a limiting current density indicated by reference numeral 60 in the scan depicted in FIG. 2.

Further cathodic increase in the applied electric potential results in no change in the reaction rate due to the limitation in supply of dissolved oxygen, thus the substantially vertical range shown in region C of the scan 28, FIG. 2. Eventually, the applied potential becomes sufficiently negative for the water reduction reaction to become operative, as illustrated at Point D in FIG. 2. As the potential becomes increasingly negative, and because of the ample availability of water in the electrolyte, the current drawn by this reaction will continue to increase, as illustrated in Region E of FIG. 2. This additional reaction is also known as the hydrogen evolution reaction (also known and referred to throughout this description as the "water reduction reaction"), and is designated on the scan of FIG. 2 by line region E terminating at point 2. This latter reaction is due to the hydrogen gas byproduct that typically forms on the cathode surface (that of the surface of the working electrode (implant 20, FIG. 1).

Figure 3:
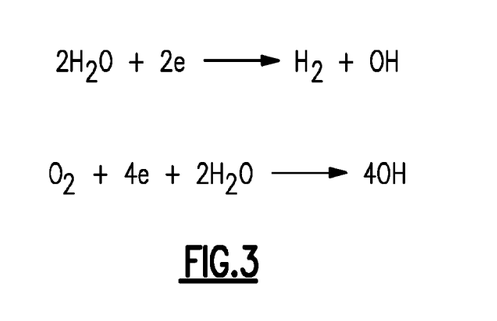
FIG. 3 shows a first electrochemical water reduction reaction equation in which 2 moles of electrons combine with 2 moles of water, thereby separating the water into hydrogen gas and hydroxide molecules, and a second electrochemical oxygen reduction reaction.

FIG. 3 represents the above described oxygen reduction and water reduction reaction formulae, respectively. Each of these reactions produces a byproduct of OH-molecules, which subsequently increases the local pH around the working electrode 32.

Figure 4:
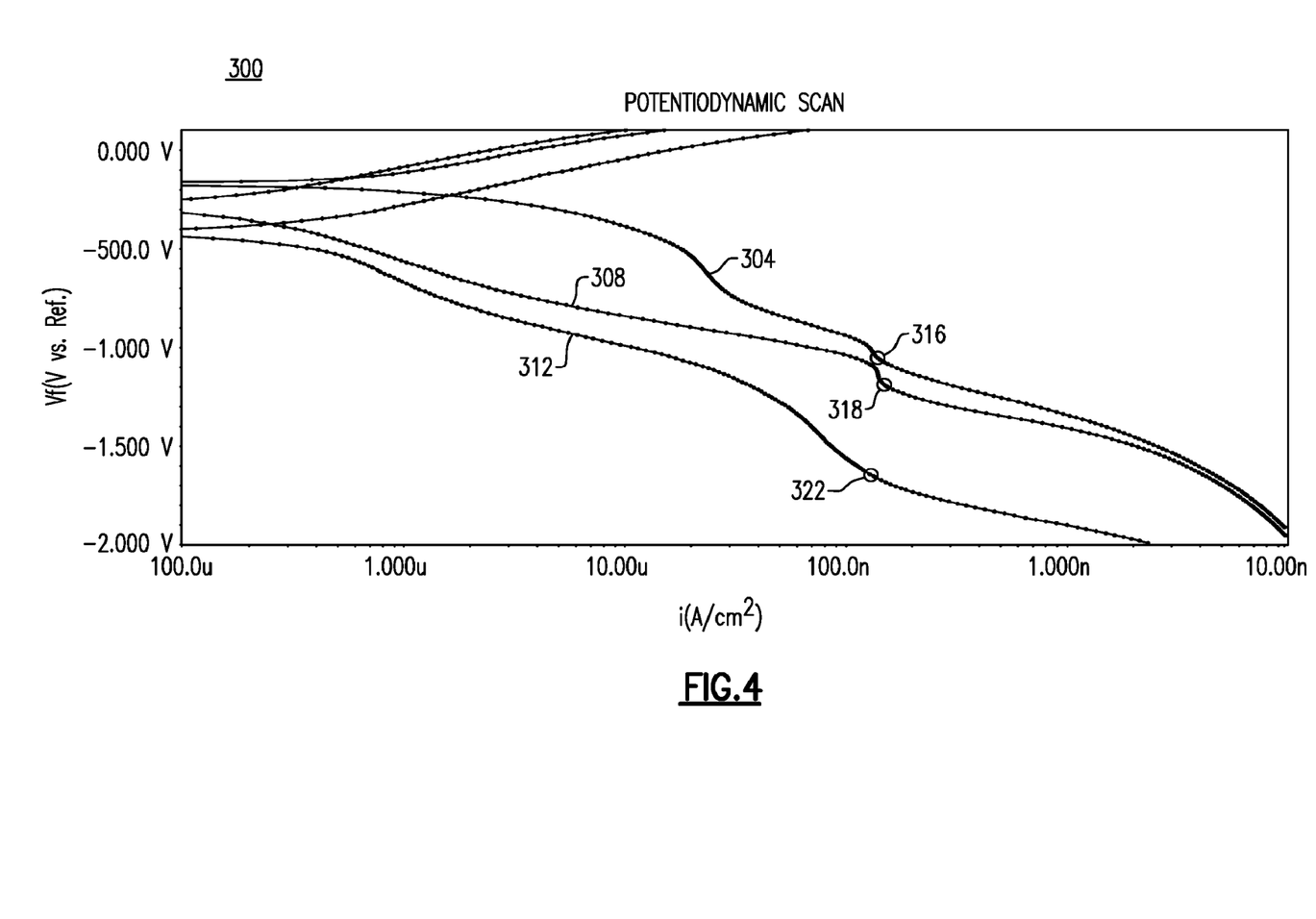
FIG. 4 is a graphical representation of superimposed cathodic polarization scans of various metallic materials, including the relative position of a water reduction reaction for each metallic material.

FIG. 4 shows exemplary polarization scans 304, 308, 312 for three (3) different biomaterials and how they are shifted differently along the current axis with respect to the voltage axis. As shown, curve 304 is that of stainless steel, curve 308 is that of cobalt-chromium, and curve 312 is that of titanium. The resulting water reduction points of each scan 304, 308, and 312 are depicted at 316, 318 and 322, respectively. It is noted that each of the disparate scans 304, 308, 312 include the same representative behavior shown in the typical scan 28, FIG. 2.

In the treatment system 10 shown in FIG. 1 and according to this embodiment, a separate device 50 is provided that is mechanically and electrically coupled, either by a wired or wireless (e.g., Bluetooth, RF, IR) connection, to the potentiostat 30. This device 50 is defined by a processor 52 that is programmed with software 54 for conducting the method and configured for controlling the application of voltage and measurement of current and voltage via the potentiostat 30 based on the detection of various controlling parameters from a polarization scan of a coupled implant 20 as described herein.

Typical potentiostats 30, such as those configured in FIG. 1, do not have the intelligence or technology to know what the surface area of the implant is and thus they prompt the users to input the surface area manually. The herein described device is linked to the potentiostat 34 and includes a processor that is suitably programmed to perform the herein described method. It will be readily apparent that a potentiostat could itself be reconfigured and further equipped with software/firmware for conducting the herein described methodology.

A plurality of challenges were defined and overcome with this invention. For example, one challenge was how to determine the surface area of the metallic object or implant which needs to be known, in order to convert the current into a desired current density. Due to the nature of the electrochemical behavior of metallic biomaterials, at some voltage ranges, current draw increases exponentially as voltage is increased linearly. Also, current draw increases linearly as exposed surface area increases linearly. Therefore, the method or algorithm cannot, in most instances, use raw current values in its calculation because that value will be scaled depending on the size of the implant. If the current is converted into current density, which is normalized for all implant sizes, then the method can readily target a specific current density. Many scientific findings related to optimal voltages for biofilm disruption are viewed in terms of current density for this reason.

The presently described device and method operate the same way as a potentiostat in terms of requiring a surface area input from the user; however, to overcome this challenge, the present invention allows for two (2) distinct modes of operation depending on whether the implant surface area is known or not. Surface area becomes more complex when taken into consideration that only the implant surfaces exposed to body tissue are considered active. One can assume all surface area of the implant (excluding the surface area of the implant located below under tight polyethylene snap connections or under bone cement, for example) can be counted as exposed surface area. The user may have information available from a database of metallic implants that contains manufacturer reported surface areas to input into the device. If this information is unavailable, the device can be suitably programmed with an alternative operating mode based from the conclusion that because current increases linearly as surface area of the implant increases linearly, the current does not need to be normalized as long as the process chooses a point along a polarization curve based on specified voltage offset from the hydrogen threshold and not quantified current. This latter mode, described in greater detail below, incorporates a cumulative coulomb-based system, as opposed to a time-based system.

Another challenge defined and overcome is that not only does the total exposed surface area need to be accounted for, but also the surface area of individual metals that may exist in the same implant. For example, a surgical metallic implant may comprise half titanium and half cobalt-chromium. However and for purposes of the inventive method, it can be concluded that a polarization scan should address this challenge naturally. The polarization scan does not use surface area ratios in its process and does not take into account which metals are exposed. It is true that each polarization scan will be shifted differently based on these ratios. Accordingly, the autonomous detection methods according to the herein described invention can make this determination from the scan and appropriately calculate the appropriate stimulation voltage.

The indicator that the electrochemical reaction on the working electrode surface has switched from an oxygen diffusion limited reaction to a water reduction reaction is an inflection point in the polarization curve 28 (FIG. 2) from near vertical to decreasing slope. The device according to this invention is programmed to detect these inflection points, and thus calculate the precise point at which the hydrogen evolution reaction occurs, which is shown as Point D in FIG. 2, and from this calculated point then increase voltage along the reaction curve to optimize current density.

The inventive technique described herein is capably of applying a potentiodynamic polarization scan 28, 304, 308, 312 to any metal or metallic implant with any combination or surface area ratio of different metallic biomaterials. As described herein, the point on the polarization scan that represents an ideal setting is chosen that determines the appropriate voltage. As described herein, the detection device 50 can be programmed in accordance with two (2) separate modes; namely a first current density mode and a second alternative cumulative charge transfer mode, each now described in greater detail.

Figure 5:
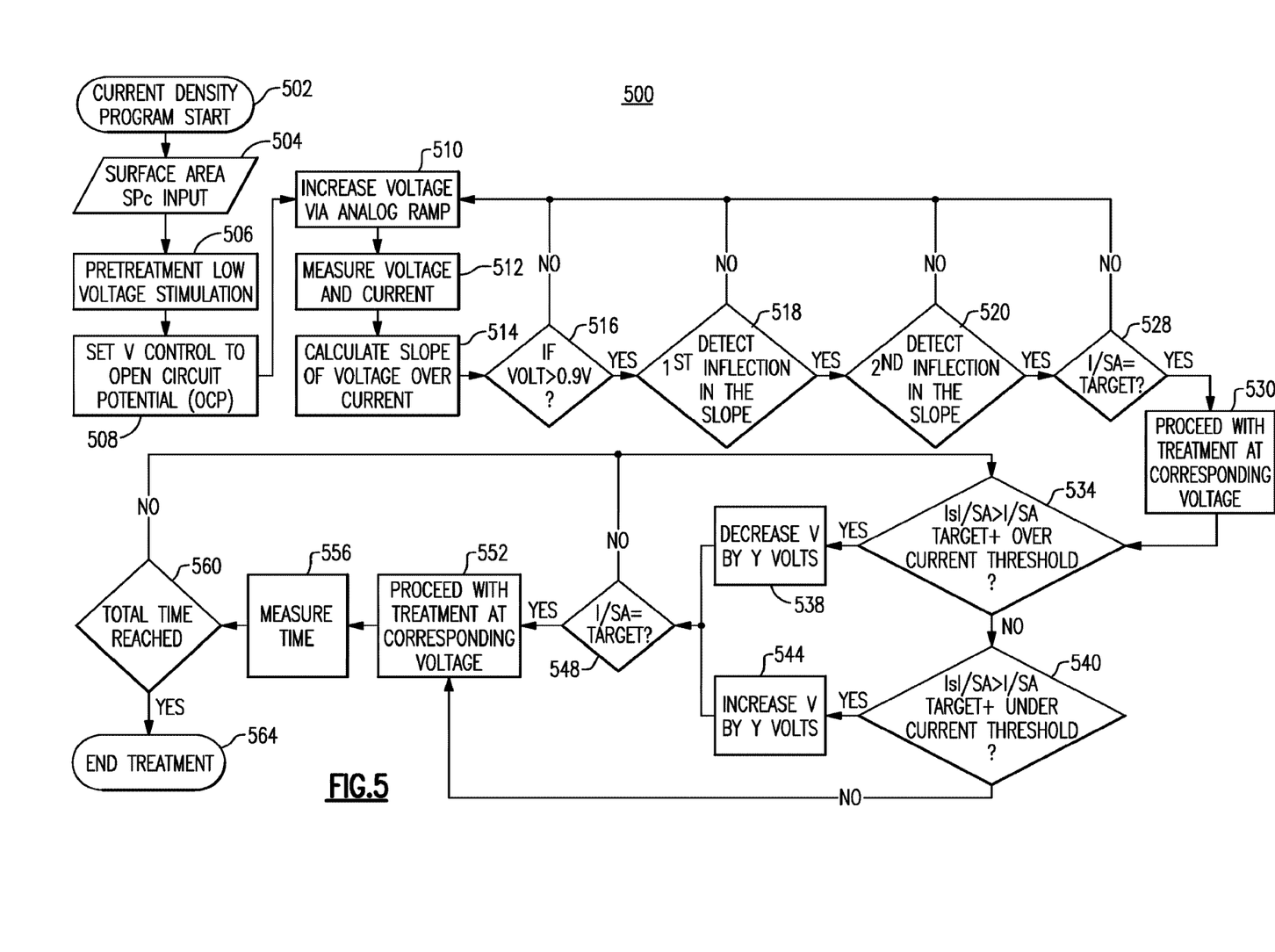
FIG. 5 is a flow chart of a voltage selecting process for use in an exemplary autonomous hydrogen evolution reaction threshold detection method based on current density.

With reference to FIG. 5, an exemplary process 500 is described based on the first current density mode, step 502. First and in accordance with this technique, per step 504, the exposed surface area of the implant is input. For purposes of this input, the physician or user may have prior knowledge of the metal of the implant based on medical records. According to the herein described embodiment, the treatment device is programmed for user input of the metal type with the device programming also preferably configured to verify the inputted metal type as a double check. Depending on the operating mode selected, the device is programmed to utilize the metal type detection differently, in order to determine the suitable treatment voltage.

Following this input, the metal implant is pretreated with a low voltage stimulation, step 506. It has been shown that implant oxide layers that have developed in the body may be more or less robust for patient to patient due to unique electrochemical environment. Therefore, when a polarization scan is performed, the natural electrochemical behaviors of a metal may become inconsistent. This situation may invariably skew scan data. To avoid this issue, a low cathodic voltage pretreatment may be used to promote consistent baseline oxide layers from patient to patient. This low cathodic voltage pretreatment is specifically less cathodic than the hydrogen evolution reaction threshold to prevent any subsequent treatment an incorrectly applied voltage and sufficiently low in magnitude that the patient does not feel the pretreatment voltage. In one embodiment, the pretreatment stimulation is −1.0V vs. Ref for 1 minute duration. However, pretreatment voltage could be any cathodic voltage ranging from open circuit potential (OCP) to −1.2V vs. Ref. for any time period ranging from 1 second to 24 hours.

The foregoing pretreatment stimulation is optional and may or may not be required for all applications. After this pretreatment step has been performed, the process can continue with a higher assurance of accuracy starting from consistently baselined oxide layers of the implant.

With continued reference to FIG. 5, the inputted metal type of the implant defines the voltage at which the hydrogen evolution reaction starts, or the threshold for hydrogen production. The type of metal is not necessarily as important as the verification that water is now being reduced, whereas in the cumulative charge transfer mode, the metal type dictates the exact voltage setting for treatment.

The method is directed to an analysis of a polarization scan graph (or curve) that will result from each material from which the implant is made. The polarization curve is created by ramping the voltage in the negative direction and measuring the resulting current over the defined range. Patient safety and comfort is optimized throughout by always incrementing the voltage during the treatment process in a smooth, analog ramp, step 510. A useful range of the polarization scan or curve is +10V to −10V vs. Ref. In one embodiment, the polarization scan will start at the metal's open circuit potential voltage (OCP), step 508, which is ramped per step 510, with the voltage and current being measured, step 512. In a preferred embodiment according to the inventive method, the resulting scan is analyzed actively, and once specific criteria are met, the scan ramps directly into the treatment voltage. In a less preferred embodiment, the scan data is computed after it has proceeded through a set voltage range, returns to OCP, and then re-ramps to the computed treatment voltage. This range (e.g., 10 volts–−10 volts) should be selected to ensure that the water reduction reaction will be contained within the cathodic polarization scan, as shown in the scans previously shown in FIGS. 2 and 4.

More specifically and during the scan, the device is programmed to detect several inflection points, which are represented by the distinctly sharp changes in slope (voltage over current) indicative of limitations or activations in certain chemical reactions at the surface of the metal implant, step 514. More specifically, a first inflection point typically occurs at about −800 mV vs. Ref within the oxygen reduction reaction, labelled B in the typical polarization scan 28 of FIG. 1. This first inflection point is not particularly helpful in the detection of the metal of the implant and therefore the device 50 is programmed according to this embodiment to disregard any inflection (change in slope) occurring anodic to −900 mV (−0.9 V), per the step 516. A second inflection point is the point of oxygen diffusion limitation. This inflection in the scan represents the point where the amount of oxygen available in the system cannot sustain any further electron transport through the system, and thus the current temporarily stops increasing. This second change of slope or inflection point, which is graphically represented by 60 in the representative scan 28 of FIG. 2 and detected according to step 518, is a first indicator of the metal type. Until this inflection point is detected, the voltage continues to gradually ramp, per step 510.

Subsequently, detection of a third inflection point, step 520, represents the initiation of the water reduction reaction, represented by section E of the polarization scan depicted in FIG. 2, and points 316, 318 and 322 of the scans depicted in FIG. 4. At this point in terms of reaction, the voltage has sufficient potential to reduce water to hydrogen ions, and thus allows for current to again increase.

While in the current density mode and once the water reduction reaction threshold has been detected, step 520, the device is further programmed to continue to ramp the applied voltage until the current density is equal to a determined target current density, per step 528, using the inputted surface area, step 504. According to one embodiment, the target current density is in the range of 0.75 to 1.0 mA/cm$^2$, in which the foregoing range has been proven empirically to be effective and safe. As previously stated, it will require different voltages to fulfill these criteria based on the alloy or alloys that comprise a metal surface of the implant 20 and accordingly this target current density is merely an example.

Upon realization of the second inflection point and target current density, a suitable working voltage is applied, per step 530. This working voltage will be applied to the implant for optimal biofilm and bacterial disruption and in accordance with a typical CVCES treatment process such as described in previously incorporated U.S. Pat. No. 9,616,142. Application of this working voltage is then maintained at the implant for a certain length of time that is typically set for treatment duration. For example, the treatment duration may be as long as 1 second to 24 hours.

With further reference to the flow chart of FIG. 5 and incorporated into the logic of the current density operating mode is a feature used to actively monitor the output voltage during steady state and adjust the voltage, if needed, in order to maintain the current density within the predetermined or target current density range. More specifically, the current density is determined by dividing the current by the surface area of the implant and if the current density is greater than the target density and over a current threshold, step 534, then the device is programmed to decrease the voltage by Y volts, step 538. Conversely and if the current density determined by dividing the current by the surface area of the implant is not greater than the target current density and under a current threshold, step 540, then the applied voltage is increased by Y volts, step 544. If the latter step indicates that the current density has maintained its target current density range, then the voltage remains unchanged and is still applied for treatment, per step 552. Otherwise, this information continuously feeds back to the time delay, step 548, so that active adjustments can be made to the voltage output per steps 538, 544, to keep the calculated current density as close to the target current density, step 548, as possible. As shown, this window's size is the target current plus the amount over the current threshold, which according to one embodiment is 200 uA/cm$^2$. However, a suitable target current density range could extend between 1 uA/cm$^2$ to 1 A/cm$^2$. In this way, the applied voltage is continuously monitored and adjusted actively in order to maintain the current density to disturb and disrupt biofilms and bacteria, while at the same time preventing damage to tissues (not shown) surrounding the metal implant.

Following adjustments as needed via steps 538, 544, and upon the target current density range is met, step 548, treatment then proceeds based on the ramped voltage, step 552. The total time for the treatment is continually measured, per step 556, and when a total time period has been reached, step 560, the treatment is discontinued, step 564.

Figure 6:
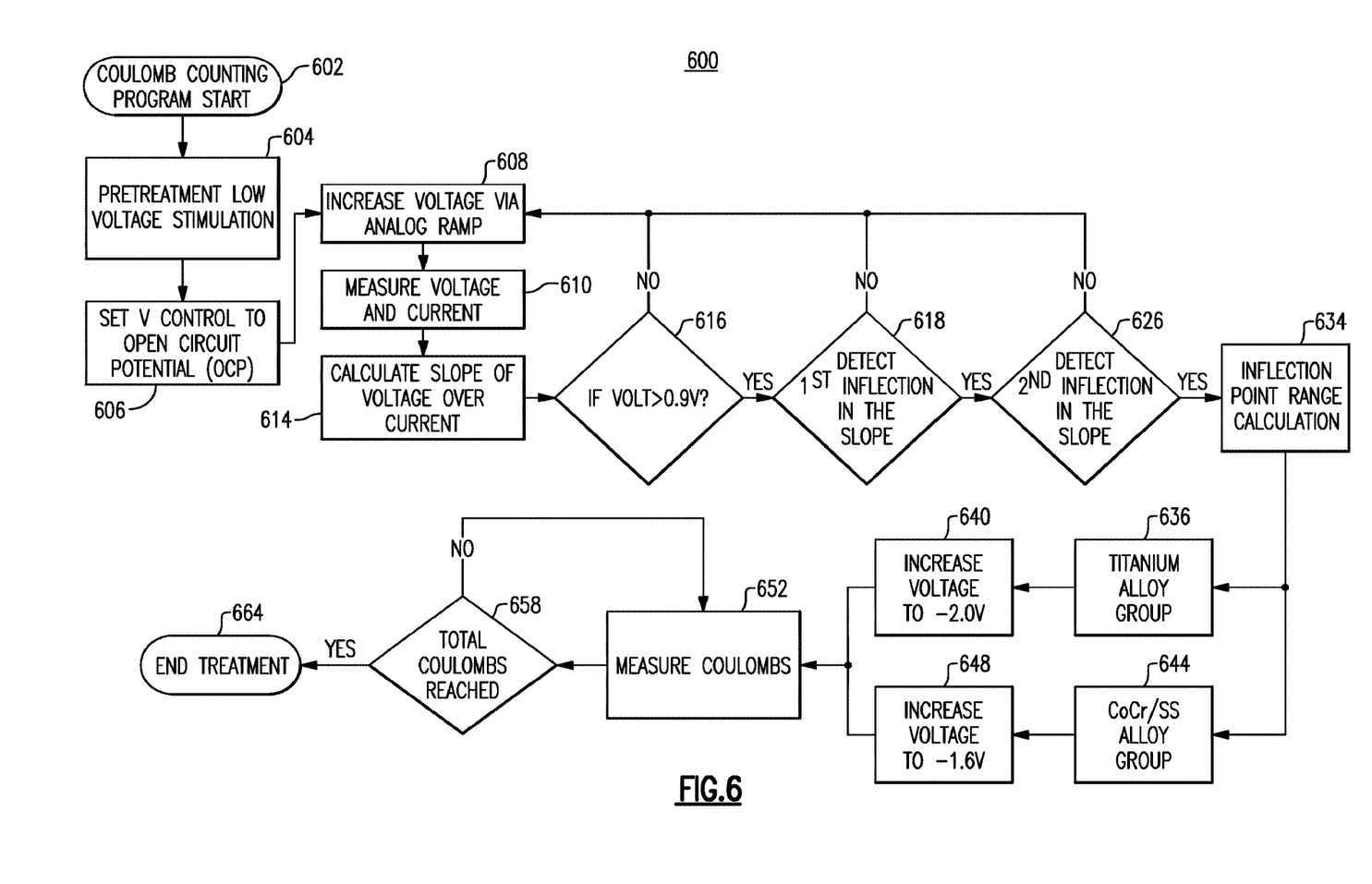
FIG. 6 is a flow chart of a process for selecting a CVCES treatment voltage in accordance with another aspect of the invention.

With reference to FIG. 6, the device is further or alternatively programmed to operate in a cumulative charge transfer mode 600. Upon initiation of this mode, step 602, an optional low voltage pretreatment stimulation similar to that previously described in the first current density mode can be applied, per step 604. Following this optional step, the voltage is initially set to open circuit potential, step 606, and the voltage is ramped in the negative direction, step 608, with voltage and current being measured, step 610, over a prescribed range (e.g., −10V to 10V) wherein the device is programmed to actively process the data through calculations that analyze the voltage to determine the slope of the resulting polarization scan representing voltage over current, step 614, as the voltage is being ramped. As previously discussed and once a determination that the voltage has exceeded the anodic voltage threshold (−0.9 V), step 616, inflection points based on slope changes can be detected on the resulting potentiometric graph, steps 618, 626 along with a range determination, according to this mode as to the amount of potential between the inflection points, per step 634.

This latter calculation step is used to determine the metal type of the implant. According to this modality, specific slope inflection points detected in the polarization curve are used to correlate the modeled behavior of a specific metal alloy in the polarization scan. This correlation is achieved by "matching" the measured voltage of each inflection point to a range of values. According to one exemplary technique, there are a series of three (3) verification steps in determining a match. According to a first verification step, the measured voltage at a first slope inflection point, representative of the oxygen reduction reaction, is compared to a specific voltage range. For titanium, by way of example, the specific voltage range varies between −1.100 V and −1.250 V. For cobalt-chromium or stainless steel, the specific voltage range varies between −0.950 V and −1.100 V.

The second verification step according to this technique is to match the range of a second inflection point representative of the water (hydrogen) reduction reaction with another specific voltage range. For titanium, the voltage range is between −1.300 V and −1.600 V, while for cobalt-chromium or stainless steel the voltage range is between −1.050 V and −1.250 V. Finally, and according to the third verification step, the span between the first and second inflection points is compared to match the range. This span is the difference in the measured voltage between the first and second slope inflection points. For titanium, the specific range varies between 0.130 V and 0.300 V. For cobalt chromium or stainless steel, the range varies between 0.030 V and 0.180 V. A successful metal type defect will be determined only if all three of the above-noted verifications are matched. If a match is not found, the metal type detected will report unknown to the user and prompt an alert. Accordingly, the device/treatment system is preferably configured to prevent further treatment to be continued.

Upon verification as to whether the implant is titanium or titanium alloy, step 636 or cobalt-chromium/stainless steel, step 644, the device is programmed to increase the applied voltage to a corresponding voltage that is predefined for that metal to be optimal for biofilm and bacterial disruption, steps 640, 648. As opposed to a time-based application, this applied voltage is then maintained until a certain amount of charge transfer is achieved, step 658. More specifically and according to one version, the device is programmed to actively calculate (i.e. count) the charge transfer in coulombs according to the relation: 1 C=1 A*1s, thereby making a coulomb calculation by measuring the current each second and then doing a summation of the charge transfer over the duration of treatment. The amount of charge transfer for biofilm disruption may be as much as 1 coulomb to 10,000 coulombs, depending on the general size of the implant. When a prescribed amount of charge transfer (coulombs) has been reached, step 658, the treatment is discontinued, step 664.

An alternative to the methods described above would be to apply the polarization scan to the implant, have users manually analyze the polarization plot or scan 28 themselves, and then select a voltage based on the manual analysis. This alternative is not preferred. First, manual analysis will introduce interpretation errors in which an error in reviewing the scans of one or more millivolts can drive significant current density differences. Second, typographic errors may easily be introduced into the analysis. Third, this technique aside from creating time delays, would also require the technology provider to educate and train users to a much higher degree to enable users to make any voltage selection-related decisions based upon a manual analysis.

The present invention addresses this issue by bringing user input to a minimal level. Autonomous hydrogen evolution threshold detection and voltage selection minimizes, if not fully eliminates, human interpretation and errors, thus providing for accuracy that could not otherwise be obtained. It also reduces the amount of education and training the user must learn and streamlines the overall treatment process in terms of efficiency and time.

Another alternative would be to apply a consistent or "one size fits all" voltage of −1.8 Volts for every type of metal because that voltage has been proven to work on titanium, which is a common metal component of orthopedic implants. This technique could result in three (3) different possible scenarios, depending on the different metals of known implants to be stimulated for treatment. The only desirable outcome would be in situation in which the implant being stimulated is made only of titanium and with the correct surface area to correlate −1.8 Volts to the optimal current density. This scenario would result in effective biofilm disruption. The other two scenarios would result from stimulating other types of metals that naturally draw higher or lower current at any given voltage than that of titanium. This stimulation would result in either a current density that is too high and thus dangerous for surrounding tissue, or a current density that is too low to effectively disrupt the biofilm. The present invention addresses this complication by autonomously analyzing the metal surface of the implant with a polarization scan to find the optimal voltage for any metal or combination of metals.

PARTS LIST FOR FIGS. 1-6

1 start point scan
2 end point scan
10 CVCES implant treatment system
20 metal implant
28 polarization scan
30 potentiostat
32 working electrode
34 counter electrode
36 reference electrode
50 device
52 processor
54 software
60 inflection point
90 electrolytic solution
300 composite polarization scan
304 curve
308 curve
312 curve
316 point
318 point
322 point
500 process
502 step
504 step 506 step
508 step
510 step
512 step
514 step
516 step
518 step
526 step
528 step
530 step
534 step
538 step
540 step
544 step
548 step
552 step
556 step
560 step
564 step
600 process
602 step
604 step
606 step
608 step
610 step
614 step
616 step
618 step
626 step
634 step
636 step
640 step
644 step
648 step
652 step
658 step
664 step
A scan section
B scan section
C scan section
D scan section
E scan section It will be appreciated by those skilled in the art that an apparatus and related method for autonomous hydrogen evolution reaction threshold detection has been described in detail herein, the method and apparatus for autonomous hydrogen evolution reaction threshold detection is not necessarily so limited. Accordingly other examples, embodiments, uses, modifications, and departures from the embodiments, examples, uses, and modifications may be made without departing from the method and apparatus for autonomous hydrogen evolution reaction threshold detection and all such embodiments are intended to be within the scope and spirit of the appended claims.

What is claimed:

1. A method of providing cathodic voltage controlled electrical stimulation comprising:
   providing a metallic object to be treated that serves as a working electrode;
   applying a polarization scan to the metallic object to be treated;
   using a processor, autonomously detecting a hydrogen evolution reaction threshold from the polarization scan to determine a cathodic voltage to be applied to the object to be treated wherein the processor is programmed to detect specific inflection points in the applied polarization scan in order to precisely detect the cathodic voltage; and,
   applying the determined cathodic voltage to the metallic object to be treated, wherein the method further comprises:
   initiating the polarization scan at an open circuit potential and scanning cathodically to a target voltage that enables the detection of the hydrogen evolution reaction by the polarization scan, followed by analyzing the polarization scan in real time; and
   detecting a first change in slope in the polarization scan indicative of an oxygen reduction reaction prior to detecting the second change in slope in the polarization scan that indicates the hydrogen evolution reaction.

2. The method according to claim 1, wherein the metallic object to be treated is an implantable medical device.

3. The method according to claim 1, further providing an anode that represents a counter electrode and in which the metallic object represents the working electrode.

4. The method according to claim 3, further providing a potentiostat so that an electrochemical process occurs on the working electrode that can be monitored.

5. The method according to claim 1, further comprising:
   measuring voltage at the first and second changes in slope in the polarization scan; and
   comparing the measured voltages to specific voltage ranges.

6. The method according to claim 5, further comprising:
   measuring the span between the measured voltages at the first and second changes in slope; and
   comparing the measured span to a specific voltage span in order to deduce the metal of the object.

7. The method according to claim 6, and upon determination of the metal of the object, further comprising:
   increasing the voltage to a specified treatment voltage upon determination of the metal of the object that is optimal for biofilm removal;
   measuring the charge transfer relative to the object; and
   terminating the treatment after the measured charge transfer reaches a predetermined level.

8. The method according to claim 1, further comprising:
   detecting a change in slope of the polarization scan indicative of the hydrogen evolution reaction;
   determining current density based on measured current and the surface area of the object following detection of the change in slope;
   comparing the determined current density to a target current density; and
   applying the voltage as a treatment voltage if the determined target current density is equal to the target current density.

9. The method according to claim 8, further comprising:
   increasing the voltage if the current density is below the target current density and a measured current is over a predetermined current threshold;
   decreasing the voltage if the current density is above the target current density and a measured current is under a predetermined current threshold; and
   comparing the current density after increasing or decreasing the voltage to the target current density.

10. A device for controlling a cathodic stimulation voltage for treatment of a metallic object, the device comprising:
   a processor configured for connection to a potentiostat;
   working, counter and reference electrodes coupled to the potentiostat, wherein the working electrode is the metallic object to be treated;

wherein the processor is programmed to:
> apply a polarization scan to the metallic object to be treated and generate polarization data;
>
> using the processor, autonomously detect a hydrogen evolution reaction threshold from the generated polarization data for determining a cathodic voltage to be applied to the metallic object to be treated for removal of biofilm wherein the processor is programmed to detect various inflection points of the applied polarization scan to determine the cathodic voltage; and,
>
> apply the determined cathodic voltage to the metallic object to be treated, wherein the processor is further programmed to:
>
> initiate the polarization scan at an open circuit potential and scan in a negative direction to a target voltage that enables detection of the hydrogen evolution reaction from the polarization data in real time; and
>
> detect a first change in slope in the polarization data indicative of an oxygen reduction reaction prior to detecting a second change in slope in the polarization data indicative of the hydrogen evolution reaction.

11. The device according to claim 10, wherein the object is a surgical implant.

12. The device according to claim 10, in which the device is separately connected to the potentiostat.

13. The device according to claim 10, in which the device is integrated into the potentiostat.

14. The device according to claim 12, in which the processor is further programmed to measure voltages at the first and second changes in slope in the polarization data and compare the measured voltages to predetermined voltage ranges.

15. The device according to claim 14, in which the processor is further programmed to measure the span between the measured voltages at the first and second changes in slope and compare the measured span to a specific voltage scan or scan range, enabling the metal composition of the object to be determined.

16. The device according to claim 15, wherein the processor is further programmed to cathodically increase the voltage to a treatment voltage following deduction of the metal composition of the object.

17. The device according to claim 16, wherein the processor is further programmed to measure the charge transfer relative to the object following the cathodical increase to the treatment voltage, and terminate the treatment after the measured charge transfer reaches a predetermined level.

18. The device according to claim 10, wherein the processor is further programmed to:
> detect a change in slope of the polarization data indicative of the hydrogen evolution reaction;
>
> determine current density based on measured current and the surface area of the object following detection of the change in slope;
>
> compare the determined current density to a target current density; and
>
> apply a suitable treatment voltage if the determined target current density is equal to the target current density.

19. The device according to claim 18, wherein the processor is further programmed to:
> cathodically increase the voltage if the current density is below the target current density and a measured current is greater than a predetermined current threshold;
>
> decrease the voltage if the current density is above the target current density and a measured current is less than a predetermined current threshold; and
>
> compare the current density after increasing or decreasing the voltage to the target current density.

* * * * *